United States Patent [19]

Lawrence, Jr. et al.

[11] 4,326,358

[45] Apr. 27, 1982

[54] HYBRIDS

[75] Inventors: Robert H. Lawrence, Jr., Tarrytwon, N.Y.; Phillip E. Hill, Hollister, Calif.

[73] Assignee: Agrigenetics Research Associates Limited, Denver, Colo.

[21] Appl. No.: 169,876

[22] Filed: Jul. 17, 1980

[51] Int. Cl.³ .............................................. A01G 1/00
[52] U.S. Cl. ........................................................ 47/58
[58] Field of Search ............................................ 47/58

[56] References Cited

U.S. PATENT DOCUMENTS

| | | | |
|---|---|---|---|
| 2,258,291 | 10/1971 | Jones | 47/58 |
| 2,522,409 | 9/1950 | Stoller | 71/2.1 |
| 2,747,334 | 5/1956 | Routinen et al. | 47/58 |
| 3,009,289 | 11/1961 | Tukacs | 47/1 |
| 3,514,900 | 6/1970 | McDade | 47/58 |
| 3,683,550 | 8/1972 | Corlett, Jr. et al. | 47/58 |
| 3,816,960 | 6/1974 | Gudin et al. | 47/58 |
| 3,821,864 | 7/1974 | Stottlemyer | 47/58 |
| 3,832,801 | 9/1974 | Carlson et al. | 47/58 |
| 3,846,937 | 11/1974 | Staba et al. | 47/58 |
| 3,955,317 | 1/1975 | Patterson | 47/58 |
| 3,972,146 | 8/1976 | Boxus | 47/58 |
| 4,003,315 | 1/1977 | Sibi | 47/58 |
| 4,038,778 | 8/1977 | Kadkade | 47/58 |
| 4,045,912 | 9/1977 | Sun | 47/58 |
| 4,052,817 | 10/1977 | Seibert | 47/58 |
| 4,060,933 | 12/1977 | Kadkade | 47/58 |

FOREIGN PATENT DOCUMENTS 1387821 3/1975 United Kingdom .

OTHER PUBLICATIONS

Encyclopedia Britannica, Macropedia, section on Fruits & Farming, pp. 761-763.
Encyclopedia Britannica, Macropedia, section on Tissues and Fluids, Plant, pp. 451-455.
Encyclopedia Britannica, Macropedia, section on Vegetables & Vegetable Farming, pp. 43-52.
Anderson et al., "Tissue Culture Propagation of Broccoli", J.A.S. Hort. Science, 102(1), 69, (Jan. 1977).
Benson et al., "Meet U.C. 157," Am. Vegetable Grower, 8, (May 1978).
Yang, "Send in the Clones," Am. Veg. Grower, 8, Oct. 1978.
Encyclopedia Britannica, Macropedia, Section on Tissue Culture, pp. 438-442.
Encyclopedia Britannica, Macropedia, section on Horticulture, pp. 1105-1114.
Encyclopedia Britannica, Macropedia, section on Plant Breeding, pp. 497-500.

*Primary Examiner*—Robert E. Bagwill
*Attorney, Agent, or Firm*—Pennie & Edmonds

[57] ABSTRACT

New hybrid seed varieties and plants therefrom are rapidly developed and commercially produced. New hybrid seeds can be readied for market in as little as three years, compared to the conventional eight to twelve years required for preexisting techniques of hybrid seed production. Plant breeders are no longer limited to homozygous parents in the production of new hybrids.

14 Claims, No Drawings

HYBRIDS

BACKGROUND OF THE INVENTION

This invention relates to the rapid development and commercial production of new hybrid seeds and plants therefrom, including melons, vegetables, grains, forages, fibre crops, and other monecious species. More particularly, it provides a technique for the rapid development of new hybrids and for the rapid commercial production of hybrid seeds.

The conventional procedures for developing new hybrids are well known and are described in the literature. The Encyclopaedia Britannica, Macropedia, has extensive sections on "Horticulture" and on "Plant Breeding." While the procedures are known and are widely practiced, their limitations are equally well recognized.

The plant breeder seeking to develop new hybrids will cross (hybridize) two parental lines where each of the lines is composed of plants which are as homozygous (purebred) as possible. Homozygosity, however, is achieved slowly; plants must be selfed (inbred) for a number of generations to obtain an essentially pure breed. From eight to twelve generations is not uncommonly required to produce lines which are sufficiently homozygous so that, when crossed with other homozygous lines, they will yield a population of genetically uniform hybrids.

Moreover, only a relatively limited number of purebred lines are available, and this restricts both the possible number of crosses and the genetic diversity of the hybrids that can be made in any given year.

Still another limitation on the development of new hybrids is that the parent plants, being reproduced sexually, may develop undesirable genetic changes from generation to generation.

A further constraint on existing techniques of hybrid plant development is the fact that many plants produce only a limited number of seeds per plant. This is particularly troublesome because inbred parental lines exhibit low vigor, which manifests itself in low seed yields. Thus, even after superior hybrids have been developed, large scale production of hybrid seed for sale may not be possible for the next year or so.

The above conditions are epitomized in the development of canning and juice tomatoes. A fair number of purebred varieties are obtainable, but due to the limitations above, only a few new hybrids appear on the scene each year.

Accordingly, a principal object of the invention is to provide a technique or method for rapidly developing, and then rapidly commercially producing, new hybrids. A further object is to produce such new hybrids from one or both heterozygous parents, and yet have the hybrid plants be satisfactorily uniform phenotypes. Still another object is to produce superior new hybrids of greater genetic diversity, and without limitation on the homozygosity or heterozygosity of the parents. Yet another object is to produce such hybrids in as little as two or three years, as compared to the eight to twelve years now required for the development and production of new hybrids. Further objects will become apparent as the description of the invention proceeds.

SUMMARY OF THE INVENTION

Briefly, in accordance with the invention, new hybrids are rapidly developed and commercially produced by combining the techniques of sexual reproduction (crossing) to develop new hybrids, and cloning (vegetative propagation) of the original parent plants to provide large-scale replication of the original crosses.

The present invention is based in part on the recognition that the crossing of genetically different individual parent plants, one or both of which is heterozygous, can on occasion yield a population of $F_1$ hybrids that, while genetically different from each other, exhibit a high degree of phenotypic uniformity (i.e., similar visible characteristics).

A further recognition embodied on the invention is that hybrid seeds derived from clones of the respective individual parents similarly yield plant populations that are phenotypically similar, as well as genetically equivalent, to the original-parent-derived F1 hybrids. Thus, where a cross of original individual parent plants (one or both of which is heterozygous) will yield phenotypically uniform original-parent-derived hybrids, crosses of clones of the parents also will usually yield phenotypically similar cloned-parent-derived hybrids.

These recognitions underlie the basic advantages of the invention. Because one or both of the original parent plants is heterozygous, the parent (or parents) can be vigorous hybrids instead of low-vigor inbreds. Consequently, the hybrid seed yield will be high.

Further, because the parental "lines" are numerically limitless, the plant breeder has available breeding "lines" of limitless genetic diversity. As a consequence, hybrids can be produced with characteristics that are equal to, or superior to, hybrids that are derived from conventional crossing of highly inbred homozygous parents. Moreover, this is accomplished with unprecedented economy.

In accordance with one aspect of the invention, a cross is made from two individual parent plants, either or both of which is heterozygous. The individual original parent plants are prepared for vegetative propagation, or cloning, using tissue culture techniques. Hybrid seeds from the crosses are planted, and if these original-parent-derived hybrid plants exhibit phenotypic uniformity, clones of the respective individual parent plants are propagated. If not, the germplasm may be destroyed. Crossing the respective clones then yields seeds of cloned-parent-derived hybrids that are genetically equivalent to the original-parent-derived hybrids, and that are themselves phenotypically similar.

In accordance with another aspect of the invention, a large number of experimental top-crosses are made between individual parent plants which differ genotypically, without regard to whether either or both is heterozygous. The individual original parent plants used in the crosses are vegetatively propagated, or cloned, using tissue culture techniques. In field trials, these large number of experimental crosses are evaluated, and a limited (small) number of optimum (i.e., best performing) original-parent-derived hybrids are selected for development. Those selected express a combination of phenotypic uniformity within the hybrid, and possess the desired hybrid characteristics. Once the selection has been made, the original individual parents of each of the selected optimum original-parent-derived hybrids are vegetatively propagated to produce clones of the individual parents of each hybrid. Then, the two cloned parent lines for each hybrid are crossed, on a larger scale, to produce seeds. Seeds produced in this manner will yield a population of cloned-parent-derived hybrid plants that are phenotypically similar to (i.e., genetically equivalent to) the optimum experimental original-parent-derived hybrids that were selected for commercialization.

A large number of experimental top crosses can thus be made, which permits the growth of a similarly large number of new experimental hybrids with unprecedented genetic diversity. This allows the plant breeder to select as parents optimum, superior, plants or sports which exhibit desirable genetic characteristics, e.g., plant vigor, growth habit, yield, disease resistance, resistance to water or salt stress, fruit or juice quality, etc. Thus, instead of being limited to a relatively small number of low vigor homozygous parental lines, the breeder can utilize any plant, irrespective of its degree of heterozygosity, in making the crosses. Indeed, phenotypically uniform hybrids have been made from F1 parents.

Once a large number of top crosses has been made, those individual crosses which demonstrate phenotypic uniformity as a population as well as desirable hybrid traits are then exploited for hybrid seed production by utilizing the cloning technique applied to their respective original parent plants. Crossing the cloned parent plants produces cloned-parent-derived hybrid seed on a large scale that is genetically equivalent to the selected optimum original-parent-derived hybrid seed.

Accordingly, crosses are made of any plants, homozygous or heterozygous, which are individually capable of being cloned. From the original crosses, a limited number of optimum original-parent-derived hybrids can be selected for further development. The individual original parent plants are then vegetatively propagated, or cloned, by tissue culture techniques to replicate the original parent plants. Crossing the cloned parent plants produces seeds for cloned-parent-derived hybrids which are genetically equivalent to the selected optimum original-parent-derived hybrids.

Genetically, the procedure of the invention can be considered to be the selection of parent plants demonstrating superior specific combining ability, and clonal replication of the parent plants followed by large-scale crossing of the corresponding clones to produce hybrid seeds that are genetically equivalent to those obtained from the original cross. The resultant cloned-parent-hybrids are phenotypically uniform, and are genetically equivalent to the original-parent-derived hybrids.

Unexpectedly, the new hybridization methodology also leads to increased seed production. The parent (or parents), being heterozygous, the parent is vigorous and exhibits a high seed yield when the parent of maximum vigor is chosen as the female. Also, clones have been found to exhibit more vigor than the original parents.

DESCRIPTION OF THE PREFERRED EMBODIMENT

Development of Breeding Strategy

As the initial step in development and production of new hybrids, a breeding strategy is formulated. Broadly stated, the goal of this breeding strategy is to cross individual plants to produce hybrids which combine desirable traits of each of the parental lines. The particular traits are, of course, defined by the commercial requirements of the market (e.g., disease resistance, yield, fruit or seed quality for edible plants, appearance for ornamentals, etc.) and the farming practice to be used.

Heretofore, the plant breeder has been required to be judicious in his selection of parental lines for crossing to produce hybrids. This is not only because the parental lines for many plants are relatively few in number, but because the cost of multiple selfings and field trial selections to develop the homozygous parent lines, and of crossings and trials to verify the quality of the hybrids, is relatively high. According to the invention, the breeder is offered an almost limitless number of parental breeding "lines," as each "line" may comprise as little as one plant which itself may be—and desirably is—a hybrid. No longer does the breeder work with breeding lines; he now can use a single plant as a breeding "line." Accordingly, the breeding strategy may take advantage of any desirable trait found in any single plant, and this plant may be crossed to any other plant to combine the desirable traits.

Stated differently, no longer is the breeder limited to a few homozygous parental lines. An outstanding individual plant, whether or not homozygous, can be crossed to a number of other plants (again, irrespective of their homozygosity) and any of the resulting hybrids which prove of value and which exhibit phenotypic uniformity can be developed and commercialized rapidly.

Moreover, the large number of different hybrids that can be developed in a single growing season permits optimum selection of superior hybrids from among them.

Selection of Individual Parent Plant

As the second step in the procedure, individual parent plants are selected. Each of these individual plants is then designated, as by physically tagging the plant, for use as parents in the subsequent crossing.

Crossing of Individual Original Parent Plants

From the original parental lines—and, again, a "line" may be even a single heterozygous plant—a large number of top crosses are made according to the desired breeding strategy. Because a particular virtue of the present technique permits the almost-endless replication of original parent plants, a corresponding large number of top crosses can be made. Thus, any desirable characteristic that appears in an individual plant may be availed of by using that plant to provide pollen to fertilize other plants, or to be fertilized by pollen from another plant, whether the respective individual plants are homozygous or heterozygous.

Accordingly, individual plants that exhibit desirable vigor, growth habit, yield, disease resistance, water stress resistance, salt stress resistance, trueness to type, or any other objectively or subjectively desired characteristic may be used for crossing. If the resulting cross exhibits the desired combination of characteristics, additional plant material (germplasm) is available for large scale duplication of the cross by cloning the parent plants. If not, the hybrid as well as its parents can be destroyed with minimal cost of time or expense.

In keeping with a preferred embodiment, a population of, say, five to twenty individual plants from within a line is chosen for crossing. This allows one line to be crossed onto several other lines, or permits several lines to be crossed onto the one. As will be apparent below, quite frequently one line contributes desirable genetic characteristics to several different hybrids.

Crossing of the individual parent plants is by conventional hybridization techniques for the species selected. Pollen from one designated individual plant (the male) is applied to the pistils of a female, which is usually an emasculated plant. Either manual pollination from the anthers of one plant onto the pistils of another, or mechanical techniques of pollen collection and fertilization, may be employed, depending upon the particular type of plant.

Obtaining Clonable Explant Tissue

After designation of the individual parent plants, and usually although not necessarily before crossing, suitable explant tissue is obtained from each of the individual original parent plants. The explant is to form the basis of vegetative propagation of the individual original parent plant, preferably by tissue culture techniques.

Obtaining explant tissue depends largely upon the particular plant. Since tissue culture propagation is preferably employed for the cloning, that part of an individual plant is selected which is capable of being developed under tissue culture conditions to increase in number and then form an entire plantlet that can be transplanted to soil and ultimately to the field. Such plant parts as axillary buds or shoot apices (e.g., for tomato plants and cabbage), curds (e.g., for cauliflower), root and stem tips, or other plant parts that can be propagated without the risk of detrimental genetic change, may be used.

Either the original parent plant itself, or normal horticulturally or vegetatively propagated counterparts, is used for obtaining clonable explant tissue for culture.

The first step in obtaining explant tissue is to assure that the plant itself is insect, disease, and fungus free. Pesticide treatment, advantageously in a greenhouse environment, may be utilized, with careful precautions being taken to assure, so far as possible, that contaminant microorganisms are excluded.

Thus, insecticides and fungicides are applied prophylactically, or the plants may be grown in isolation.

A few days prior to obtaining explant tissue, the plant and plant area are prepared for excision to remove the explant. The plants are desirably sprayed with a fungicide solution, which is also administered to the soil surrounding each plant.

Immediately prior to obtaining the explants, the plant tissue area is sterilized with an appropriate antiseptic or aseptic agent, advantageously a 70% ethanol-water solution. Sterile scalpels, forceps, and gloves are used for the actual excision and for the transfer of explant tissue to the tissue culture facility.

Desirably, several explants are taken from each plant. While the tissue culture techniques that are presently available result in high survival rates, it is advantageous to insure the availability of germplasm of an individual plant by obtaining sufficient explants to protect against chance mortality.

From this point onward, aseptic laboratory conditions must be maintained for the cloning. The nutrient medium for propagating plants must itself be sterile, as the medium will in most instances favor microorganism growth. Accordingly, the laboratory area is maintained sterile, and all transfers of vegetatively developed shoots or other material is effected in a germ-free environment.

Optional Storage of Explants or Shoots

Because at least one, and usually at least two, generations are required for the development and commercial production of new hybrids using the present methods, it is necessary to maintain the germplasm of each parental line intact for a corresponding length of time before actual commercial production. Thus, the explant tissue, or other forms of tissue cultures such as shoots developed from explant tissue, must be preserved genetically intact during this period.

With perennials, the plant itself may be grown in isolation for several years, and explants removed at any time. This is the simplest procedure, and is optimum practice when it can be effected.

For plants having only one or two growing seasons, either of two alternate approaches can be taken. First, an explant or cutting can be vegetatively propagated, and the propagation repeated every several weeks, or as frequently as necessary, in order to insure a supply of shoots when it becomes necessary to produce more hybrids from clones of the original parents.

A second procedure, which has not been sufficiently developed at present, is to utilize cryogenic techniques to store and preserve either explants or shoots. Ideally, liquid nitrogen temperature should permit such storage for months or even years. Others have utilized low temperature storage, e.g. Seibert U.S. Pat. No. 4,052,817, with various disclosed cryoprotectants added to prevent tissue damage.

Cloning Explant Tissue

The explants or cuttings removed from individual parent plants are then propagated vegetatively, or cloned, under tissue culture conditions so as to produce a number of plantlets, each genetically similar to the present genotype.

Tissue culture techniques are, in a broad sense, widely developed. State-of-the art technology is reviewed in "Propagation of Higher Plants Through Tissue Culture," Proceedings of International Symposium, University of Tennessee, Knoxville, Apr. 16–19, 1978 (Technical Information Center, U.S. Department of Energy, National Technical Information Service, U.S. Department of Commerce, Springfield, Va. 22161, Conference-T80411). See also the article on "Tissue Culture" in the Encyclopedia Britannica, Macropedia, and the articles therein on "Plant Breeding," "Horticulture," "Tissues and Fluids, Plant," "Fruits and Fruit Farming," and "Vegetables and Vegetable Farming." Other references are cited elsewhere herein.

In substance, a part of a plant is caused to grow or multiply, or both, in vitro under sterile conditions, in a preferably synthetic nutrient medium. The composition of such medium includes: inorganic ions necessary to maintain normal fluid balance and to act with certain enzymes; energy sources such as sucrose, which also supply a major source of carbon atoms for forming cell constitutents; nitrogen-containing compounds such as amino acids which are the basic building blocks for proteins of the cell; essential vitamins; certain hormones such as auxins and/or cytokinins for growth of particular plant structure and the like. Nutrient media are described, for example, in standard references by Murashige and Skoog, Skoog, Heller, Knop, Gamborg, White, and Street.

An agar gel medium is advantageously employed for in vitro cloning, especially when using organogenetic methods. Gel propagation methods as well as the less-desirable liquid suspension (shake) culture technique are described, for example, in E. Thomas and M. R. Davey, "From Single Cells to Plants," (Wykenham Pupl. 1975), and in D. N. Butcher and D. S. Ingram, "Plant Tissue Culture," (Camelot Press, 1976).

Depending on the particular plant, different in vitro techniques have been found to be desirable. For tomatoes, as set forth more fully below, a three stage technique is employed; in the first stage, or initiation, shoot cultures are established from axillary buds in a basal medium containing a low concentration of an auxin; in the second, multiplication, the nutrient medium contains a higher concentration of auxin so as to permit the growth and development of the shoots which are generated in the initiation stage; in the third, root development, a higher auxin content is utilized. A similar three stage procedure has been found desirable for cauliflower (see application Ser. No. 169,874 filed concurrently herewith), and for broccoli (see W. C. Anderson and J. B. Carstens, "Tissue Culture Propagation of Broccoli, *Brassica Oleracea* (Italica Group), for Use in Fl Hybrid Seed Production," J. Amer. Soc. Hort. Sci., 102(1), 69–73 (1977). A single stage cloning protocol is sufficient for cabbage (see application Ser. No. 169,875 filed concurrently herewith). Other tissue culture procedures are either known or may be developed for other plants.

In a typical protocol, represented by tissue cloning techniques developed especially for tomatoes, a three stage procedure is utilized. Approximately 10–20 axillary buds aseptically removed from each parent plant are grown in an initiation medium for about 4 to 5 weeks. Each bud forms a shoot under these conditions.

At the end of this time, the shoots are removed from the agar medium, and axillary buds from the shoots are again carefully removed, with the aid of a stereomicroscope. The buds are then transferred to a multiplication medium, where, within a month or so, each bud grows into a shoot possessing approximately three or more additional buds. The buds are then separated, and transferred either to a third medium where, at a high auxin content, root development proceeds and a complete plant is formed, or to another cycle on the multiplication medium for further increase in number.

Finally, when sufficient plants are available from culture, they are separated and transferred to a greenhouse for development into normal-appearing plants which are in fact clones of the original parent plants.

Selecting Optimum Hybrids

When the original experimental hybrids derived from the individual parent crosses have grown to maturity, it is possible to select from among the hybrids a limited, small, number of optimum hybrids which exhibit the desired characteristics.

First, the population (typically from 25 to 200 in number) of hybrid plants from each individual cross is examined for uniformity of phenotype. Those crosses whose populations show a high degree of phenotypic uniformity within the individual cross are selected for further evaluation. Those crosses that shown significant phenotypic segregation (non-uniformity) are discarded.

Those hybrids that have passed the above test are now examined for hybrid vigor, disease resistance, yield, plant and fruit quality, and other characteristics that are desired in cultivars having maximum commercial utility.

In the case of tomatoes, tomato shape and the quality of the fruit and fruit juices are the prime considerations. Other factors, such as wilt resistance, salt tolerance, and the like also enter into consideration in selecting optimum (original-parent-derived) hybrids.

An additional factor, of particular importance when the hybrids are to be harvested mechanically, is concentration maturity, that is, the extent to which all members of the population mature at approximately the same time. This becomes important when there is no opportunity to manually select or reject fruit for harvesting.

Once the small number of optimum (original-parent-derived) hybrids has been selected from among the large number of experimental hybrids, vegetative propagation of the individual original parent plants of each of the selected optimum hybrids is commenced. All other germplasm of un-selected parent plants—whether the plant itself, cuttings, explants, or shoots—may then be discarded.

Clones of the individual original parent plants of each of the selected optimum experimental (original-parent-derived) hybrids are then propagated and multiplied to provide a large number of clones, one set of clones corresponding to each of the two original parent plants of each selected hybrid. The procedures of propagation and multiplication were described earlier above, and are specified in more detail for one representative species, tomatoes, below.

Crossing Cloned Parental Lines

Having vegetatively propagated each of the individual original parent plants of each of the selected optimum experimental original-parent-derived hybrids, it is now possible to cross the cloned parent plants to produce seeds of cloned-parent-derived hybrids. These cloned-parent-derived hybrids are genetically equivalent to the original hybrids inasmuch as clones of the original parents are genetically equivalent to the original parents themselves.

The procedure used to cross the cloned parent plants to produce seeds of cloned-parent-derived hybrids parallels that of crossing the original parent plants to produce experimental original-parent-derived hybrids. The main difference, of course, is that many clones are now available corresponding to the respective original parent plants.

For optimum practice, pollen from clones of the original parent plant that had been used to provide pollen for the crossing of individual original-parent-derived hybrids is utilized in the crossing of cloned parental lines. Correspondingly, clones of the plant that had been the female member of the pair are used as females in the crossing of the clones.

Procedurally, and depending primarily on the type of plant involved, the larger-scale production of hybrid seed from cloned parents is accomplished in the same manner as was used for production of original-parent-derived hybrids in the first instance. The scale, of course, is much greater, depending on the amount of hybrid seed that is required.

Verification by Field Trials

Plants within an individual hybrid population must have an acceptably uniform phenotype to be of significant commercial interest. (Genetic uniformity, of course, is not achievable unless both parents are homozygous.) Phenotypic similarity manifests itself in gross visible characteristics of the plant population, but other criteria may also be present. In hybrid processing of tomatoes and other mechanically harvested plants, one important measure of phenotype uniformity is essentially simultaneous maturation (concentration maturity) of all plants within the hybrid population.

When the procedure of the present invention is followed, in theory at least all plants within a population of cloned-parent-derived hybrids are phenotypically similar to each other and are genetically equivalent to the original-parent-derived hybrid. Since only those original-parent-derived hybrids were selected that exhibited phenotypic uniformity, it can be expected that phenotypic similarity will exist among the cloned-parent-derived hybrids. In practice, however, in view of the large expenditures involved in producing and then using hybride seed, it is economically desirable to verify phenotype uniformity by field trials.

Field trials (pilot production) are conducted on a semi-commercial scale to verify the genetic equivalence between cloned-parent-derived hybrids and original-parent-derived hybrids, as well as to verify the phenotypic uniformity of plants within the population of cloned-parent-derived hybrids.

Field trials to verify the equivalences are conducted using hybrid seeds obtained by crossing clones of the respective original parent plants, on a sufficient scale to provide the quantity of seeds necessary for field trials. Success of the field trials verifies success of the combined crossing and cloning procedure of the present invention.

At the field trial level, performance of the selected hybrids can be monitored, and any problems can be detected before full scale commercial production begins. If the problems are sufficiently serious, then the hybrid strain can be discarded along with its parental material.

Commercial Production

Once cloned-parent-derived hybrids have been grown to maturity and harvested to provide for precommercial verification in the field trials, full scale commercial production of hybrid seeds can begin.

The procedures of cloning the individual original parent plants by vegetative propagation that were described earlier are repeated to obtain additional cloned parent plants. The clones of the respective original parents are then crossed to produce large quantities of hybrid seed for sale.

In succeeding productions, additional clones of the individual original parent plants are propagated to provide germplasm for producing the next generation of cloned parents for crossing to produce seeds of cloned-parent-derived hybrids. These similarly are genetically equivalent both to the prior generation of cloned-parent-derived hybrids and to the original parent-derived hybrids.

Applications

The technique of the present invention is applicable to a wide variety of monecious crops. Provided only that parent plants can be cloned, and that the germplasm can be maintained over a number of generations, any plant which is susceptible to hybridization can be used in the production of new hybrids.

Vegetable crops are particularly valuable candidates for this method of new hybrid production. The high cost of seed, the frequent low seed yield per plant, quickly shifting disease and pest patterns, and the economic value of superior cultivars, favors the rapid development and commercial production of new hybrids. Tomatoes are especially important, and are exemplified herein.

Other garden crops such as melons likewise may be treated according to the present invention. The potential improvement is great for each of these agricultural species, and there is a demand for new and better varieties of each.

Other vegetables, particularly the Brassica species of cauliflower, cabbage, and the like, similarly may be improved by the formation of new hybrids and their rapid development according to the invention.

Economically, cereals do not appear to be a prime candidate for the invention herein, although the process is applicable. For some plants such as rice, there may be too few seeds per plant for the system to become economic, and for other cereals the value of hybrids as compared with preexisting plant varieties may not be large.

In substance, therefore, the technique of the invention provides a method of rapidly developing and commercially producing new, commercially useful, hybrids from the crossing of individual plants that need not be homozygous. It comprises the steps of (a) crossing pairs of selected individual original parent plants to produce experimental original-parent-derived hybrids, (b) selecting optimum original-parent-derived hybrids that exhibit both phenotypic uniformity and useful hybrid characteristics, (c) cloning, by vegetative propagation, each of the individual original parent plants of each of the selected experimental original-parent-derived hybrids so as to obtain cloned parent plants, and (d) crossing the cloned parent plants to provide seeds for cloned-parent-derived hybrids that are genetically equivalent to the selected original-parent-derived hybrids.

EXAMPLE (TOMATOES)

In this Example, tomatoes were crossed to develop four new hybrid varieties. Their respective parents were clonally propagated, and crosses of the clones were made. Each of the four hybrid varieties exhibited a population of uniform phenotypes and demonstrated yields, maturity concentration, fruit quality factors, and plant habits equal or superior to the best presently (1979) known varieties.

Selection of Individual Parent Plants

Initially, sixty lines and/or cultivars of tomatoes were chosen, each differing genotypically from any other. Many of the lines were heterozygous, and in some instances were $F_1$ hybrids. Seeds from these lines were planted in greenhouse flats to establish a population of from 100 seedlings, from which a small number of individual plants (e.g., one to ten) of each were selected. Each of these individual plants was then designated, by physical tagging, for use as a parent in the subsequent crossing. 144 individual parent plants were so designated, and were chosen as genotypes for hybridization.

Crossing of Individual Parent Plants

A large number of crosses were made from the selected 144 individual parent plants. The objectives of the crossing strategy were to obtain tomatoes having the desired characteristics of fruit shape and quality. Thirteen major classifications based on fruit morphology were utilized; e.g., shape being square round to square round, square round to blocky, round to round, elongated to elongated, blocky to round, etc.

The pollen from an individual designated male plant within a line was then crossed to several designated individual (emasculated) females. Conventional manual pollination techniques were employed, using pollen from multiple flowers in one designated individual plant to fertilize multiple emasculated flowers on a designated female plant.

The resulting tomatoes from each specific cross were harvested, and the seeds were collected.

Seeds from each specific cross were planted in field trials for comparison testing; approximately fifty-to-one hundred plants from each cross were thus planted. Cultivation was by conventional farming techniques typical for the area.

At the appropriate stage of maturity, data were collected with respect to pathogen resistance, vigor, fruit shape, number of fruit per plant, and other factors identified below.

It was ultimately found that, of the original large number of crosses, four hybrids were outstanding. These were:

(a) 6290-5×6269-2; Fusarium Race II Resistant Early Round, obtained by top-crossing a single plant out of a breeding line obtained in the $F_5$ from the University of California (Davis) onto a single plant from GS 12 Hybrid (Goldsmith).

(b) 6240×6238-2; Fusarium Race II Resistant Medium Early Square Round, a single plant out of the variety of U.C. 82A crossed to a single plant of Keystone Exp. 9976.

(c) 6274-2×6250-2; Fusarium Race II Resistant Medium Late Square Round. This was obtained from a single plant out of the $F_1$ of the cross between Keystone Exp. 9976 and a U.C. (Davis) breeding line, crossed to a single plant out of an $F_7$ breeding line (Keystone) derived from a long fruited 198 type crossed to Keystone super concentrated material.

(d) 6276-2×6250-2; Fusarium Race II Resistant Medium Maturity Square Round. A single plant out of the $F_1$ of the cross between U.C. (Davis) breeding line and a Keystone breeding line out of an unknown parentage crossed to the same $F_7$ breeding line used in the immediately preceding cross.

A semi-quantitative inspection of tomatoes from the various crosses is given below.

tyric acid 1 mg/l, and (c) the agar concentration was increased 1% to withstand shipping.

Upon arrival at the tissue culture facility a week later, the cuttings were removed from the culture tubes and placed in moist sterile potting soil (1/1 peat/perlite) in a temperature controlled greenhouse. Plants grown from these cuttings were those actually used as a source of the explant tissue for culture establishment.

Several precautions were taken in growing the plants in order to obtain sterile, disease-free plants for subsequent tissue culture. To keep the plants free from insects at all times, pesticides were employed; alternatively, if an insect-free greenhouse is available, the plants can be grown in isolation. Fungicides were prophylactically applied where warranted.

Approximately two days prior to taking explant tissue, the plants were sprayed with a fungicide (Physan 20, Consan Pacific, Inc., Whittier, Calif., 2.6 mg/l), and 0.5–1.0 mg/l of the same solution was applied to the soil surrounding each plant. This was repeated one day before taking explant tissue.

The procedure selected for clonal propagation was multiplication of axillary buds. Desirably, about ten buds were taken from each plant. To collect these buds, the plant tissue area was first sprayed with a 70% ethanol solution, and the bud area was excised with a sterile scalpel. The tissue was thereafter handled with sterile forceps or gloves washed with 70% ethanol, and was placed in culture tubes containing sterile water.

Sterilization of the explants was effected by treatment with a sodium hypochlorite solution (20% Chlorox) containing a surfactant (Tween 20, 2 ml/l). The solution and tissue were agitated for about 30 seconds, and then placed in a vacuum dessicator; 30 cm mercury vacuum was applied for 15 minutes to insure complete contact with the sodium hypoclorite.

After vacuum treatment, the solution was decanted and rinsed three times with sterile distilled water, agitating between each rinse.

Damaged tissue was then aseptically removed, and

| | | HYBRID PROCESSING TOMATOES | | | | | | | |
|---|---|---|---|---|---|---|---|---|---|
| | | FRUIT QUALITY | | | | SHAKING TEST** | | | |
| RATING | VARIETY | SHAPE OF FRUIT | VISCOSITY | pH | SOLIDS | NO STEM | W/ STEM | GREEN | SHATTERED & ROTTEN | TOTAL RED FRUIT |
| XX | 6290-5 × 6269-2 | Round | 99.4 | 4.23 | 6.24 | 21½ | 35 | 9½ | 2½ | 56½ |
| X | 6240 × 6238-2 | Square/Round | 236.3 | 4.36 | 4.90 | 83 | 7 | 21 | ½ | 90 |
| XX | 6274-2 × 6250-2 | Square/Round | 292.7 | 4.41 | 5.26 | 33¼ | 26¼ | 59½ | 2½ | 59½ |
| XX | 6276-2 × 6250-2 | Square/Round | 231.0 | 4.27 | 5.08 | 23¾ | 35¾ | 47 | 2½ | 58⅝ |
| | 7879 K3* | Round | 138.5 | 4.30 | 5.3 | 32⅝ | 29½ | 16¾ | 6 | 62 |
| | GS-12* | Round | 224.0 | 4.38 | 5.78 | 12½ | 18¾ | ¾ | 2½ | 31¼ |
| | GS-9* | Plum | 311.7 | 4.44 | 5.75 | 56½ | 4¾ | 4 | 7¾ | 61¼ |

*These results represent data from several replications remote from the experimentals and thus are indicative only.
**This is an empirical simulation of mechanical harvesting. "No stem" and "total red fruit" are desirably maximized.

Obtaining Clonable Explant Tissue

After designation of the individual parent plants, the parent plants, while in the seedling stage in the greenhouse, were prepared for obtaining clonable explant tissue. From one to four cuttings of each of the parent plants were obtained, without surface sterilization, and were prepared for protected shipment to the tissue culture facility. The cuttings were placed in culture tubes containing an agar media similiar to that described below for clonal propagation, except that (a) vitamins and sucrose were omitted, (b) the auxin was indolebuthe axillary buds were placed on an sterile agar medium described below for culture initiation.

Optional Storage of Explants or Shoots

Two different methods have been employed to maintain the germplasm of the individual parent genotypes over a period of several generations.

In the first, a small bank of greenhouse plants was established from the cuttings of each individual parent plant. All plants were kept insect and disease free.

In the second method, a bank of twenty to thirty cultures of each genotype was maintained by serial transfer of shoots, as described in the section on cloning, below.

With either procedure, once it was ascertained that seven individual parent genotypes were to be replicated by clonal, or vegetative, propagation, the other 137 genotypes were discarded.

Cloning Explant Tissue

Cloning was effected in three stages—initiation, multiplication, root development—each under selected tissue growth conditions. First, cultures were established on an initiation nutrient medium containing a low concentration of indoleacetic acid (IAA), and were permitted to grow for four to five weeks. A single shoot developed from each bud.

Axillary buds excised from each of the shoots derived from the initiation stage were then transferred to the second stage, or subculture, for multiplication. This was effected in a nutrient medium which contained a higher concentration of IAA, and permitted the growth and development of shoots from each of the axillary buds obtained in the initiation stage. Multiplication was achieved by growing the axillary bud into a fully developed shoot within the culture tube, and thereafter excising from that shoot each of the axillary buds which developed on the shoot. The individual buds were then placed in separate tubes to produce a new shoot from each bud. Multiplication can be repeated every four weeks or so as needed.

When sufficient shoots (clones) were available from the multiplication stage, the third culture stage was employed. This utilized a higher IAA content in the nutrient to develop the roots on each shoot.

The following was the basal nutrient gel medium composition:

| Medium Composition for In Vitro Culture of Tomato | |
|---|---|
| Constituents | mg/l |
| Inorganic Salts | |
| Murashige and Skoog Salt Formulation | a/ |
| NaH$_2$PO$_4$ . H$_2$O | 170.00 |
| Iron Complex[b/] | |
| FeSO$_4$ . 7H$_2$O | 27.85 |
| Na$_2$EDTA | 37.25 |
| Vitamins | |
| Nicotinic Acid | 0.50 |
| Pyridoxine . HCl | 0.10 |
| Thiamine . HCl | 0.50 |
| Hormones | |
| 3-indoleacetic acid (IAA; Auxin) | 0.03–3.00 |
| N$^6$-furfuryladenine (Kinetin) | 0.03 |
| Ancillary Organics | |
| Glycine | 3.00 |
| Inositol | 100.00 |
| Sucrose | 30,000.00 |
| Agar (Sigma Grade IV) | 7000.00[c/] |

[a/] T. Murashige and F. Skoog, "A revised medium for the rapid growth and bioassays with tobacco tissue culture," Physiol. Plant., 15, 473–497 (1962).
[b/] Maintained as fresh stock solution.
[c/] pH at 5.7 prior to autoclaving 15 min. at 121° C. at 16–18 psi. 20 ml media/culture tube 25 × 150 mm.

In more detail, the sterile axillary buds excised from the individual designated parent plants (or indirectly from their cuttings) were first transferred to an initiation medium comprising the basal medium in the table above, containing 0.03 mg/l of indoleacetic acid (IAA) as the auxin, and allowed to grow for about four to five weeks prior to subculture.

After this growing period, the shoots were individually removed from their cultured tubes and, under sterile conditions, the axillary buds were then carefully excised from each shoot.

These buds were then transferred to a multiplication medium, having the composition set forth above, with the exception that the IAA content was 0.3 mg/l. In four weeks, each axillary bud developed into a shoot having approximately two to seven axillary buds, although this is highly variable.

The multiplication cycle was repeated every four weeks or so, in each case removing the developed shoot, excising the axillary buds, and repeating the initiation and multiplication stages for additional shoot proliferation. When the original-parent-derived hybrids have grown sufficiently to permit selection of a small number of optimum hybrids, as described previously, a determination was made as to which individual original parent plants yielded optimum hybrids. In the Example described herein, seven such individual plants were identified. Germplasm of the seven was maintained, while shoots from the remaining 137 plants were discarded. Germplasm of these seven specific parents was retained for further multiplication.

When sufficient numbers of axillary buds from the seven selected original parent plants were available, the respective shoots were transferred to a third medium containing 3.0 mg/l IAA for root development. After two weeks, the cultured shoots showed good root development, and the plantlets were ready for transfer from tissue culture conditions to the greenhouse.

During the initiation and during the multiplication stages, temperatures of 25°±3° C., and light intensity from cool white fluorescent bulbs of 3500 lux was maintained, with a photoperiod of 16 hours. For root development, a light intensity of 6,000–10,000 lux was used.

The conditions above are apparently genetically conservative, in that virtually no phenotypic variants were observed. The conditions permit germplasm to be maintained as a bank by repeated serial transfer in the multiplication medium, and permit crossing of the cloned plants for several years in succession.

Planting of Plantlets

The plantlets, or rooted shoots, obtained from the final stage of clonal tissue culture were then carefully planted in controlled growth rooms. For each selected parent genotype, a greenhouse ground bed was thus established containing 48 plants cloned by the above procedure from each of the original seven parent plants.

The plantlets were first removed from their culture tubes, agar was washed from the roots, and then planted approximately 10–15 mm below the root collar in moist peat/vermiculite in seedling trays (2 inch by 2 inch cells). Trays were placed in plastic tubes to control moisture loss, and were maintained in growth rooms at 28° C. and 16 hour photoperiods of 1500–2000 lux from cool white fluorescent bulbs.

After two days in the growth rooms, the plastic tubes were opened to harden off the plants, and the tubes were fully removed three days later. After an additional three days in the growth room, the plants were transferred to seedling trays in a greenhouse in full sunlight.

Following one week of growth in the greenhouse seedling trays, the plants were transferred to greenhouse ground beds to produce cloned parental lines of each of the respective individual parent plants.

Crossing Original Parent Plants

As indicated previously, top crosses were made utilizing the 144 individual original parent plants.

Conventional tomato crossing techniques were utilized. For each cross, the flowers on one plant were emasculated by removal of the anthers before the pollen grains had developed. Fertilization was effected by collecting pollen from multiple flowers on the other (male) plant and manually distributing it onto the pistils of the emasculated (female) member of the pair.

The female plant was then permitted to develop tomatoes to maturity. Tomatoes from each female were collected, and the seeds thus obtained constituted the hybrid seeds for planting in field tests.

In a refinement of the above procedure, several individual parents from within each parental line are initially chosen. The most vigorous parent from each line is then crossed to the most vigorous parent of another line.

Hybrid seeds thus obtained are subjected to a field test procedure, as described previously, to ascertain whether the hybrids, as a population, possess the desired genetic characteristics.

Crossing Cloned Parental Lines

The procedure of crossing cloned parent plants to produce seeds of cloned-parent-derived hybrids parallels that of crossing the original parent plants to produce experimental original-parent-derived hybrids. The only difference, of course, is that many clones are now available corresponding to the respective original individual parent plants.

For optimum practice, pollen from clones from the original parent plant that had been used to provide pollen for the crossing of individual original parent plants is utilized in the crossing of cloned parental lines. Correspondingly, clones of the plant that had been the female member of the pair are used as females in the crossing of the clones. The same technique of manual emasculation of one plant and fertilization (either manually or with insects) with pollen of the other as was used for the original crossings is followed.

The preferred technique is the obtaining of pollen from clones of the plant that contributed pollen from the original crossing, and the corresponding use of emasculated clones of the plant that was the original pollen receptor. While this may, in theory, be unnecessary due to the reciprocity rule of plant genetics, it is the preferable approach in order to minimize any chance variations. In practice, the more vigorous parent will usually be employed as the female to maximize seed yield.

Verification By Field Trials

Before full scale commercial production of hybrid seeds can begin, it is highly desirable that semi-commercial field trials be conducted to verify the genetic equivalence between cloned-parent-derived hybrids and original-parent-derived hybrids. Thus, should it happen that for some inexplicable reason the hybrids obtained by crossing the clones are not of a quality corresponding to those obtained by crossing the individual original parent plants, commercial development of the hybrid can be abated.

Field trials to verify the equivalency are conducted using hybrid seeds obtained by crossing clones of the respective original parent plants, on a sufficient scale to provide the quantity of seeds necessary for field trials using commercial harvesting equipment. Any problems that occur can then be detected before full scale commercial production begins.

Commercial Production

Once cloned-parent-derived hybrids have been grown to maturity and harvested to provide for pre-commercial verification, full scale commercial production of hybrid seeds can begin.

The procedures of cloning the individual original parent plants by vegetative propagation that have been described earlier are repeated to obtain additional cloned parent plants. The clones of the respective original parents are then crossed to produce large quantities of hybrid seed for sale.

In the examples given heretofore, commercial hybrid seed production was accomplished by crossing two cloned-parent lines. For the purposes of this invention it is only necessary to clone those parent lines that are not homozygous (heterozygous). If one line should happen to be homozygous, it can be grown from seed or cloned. All heterozygous parent lines must, however, be clones of the original experimental parent plant.

We claim:

1. A process for rapidly developing hybrids and commercially producing hybrid seeds, comprising:
   (a) selecting a first parent plane and a second parent plant;
   (b) crossing said first parent plant with said second parent plant to obtain original-parent-derived hybrids that are phenotypically uniform;
   (c) cloning said first parent plant to produce a first cloned parental line; and
   (d) crossing plants of said first cloned parental line with said second parent plant or with a second parental line produced therefrom to obtain hybrid seeds which yield hybrids that are phenotypically uniform, provided that when said second parent plant is heterozygous and a second parental line produced therefrom is used in the crossing of step (d), said second parental line must be produced by cloning.

2. The process according to claim 1 wherein said second parent plant is heterozygous.

3. The process according to claim 1 wherein both of said first and second parent plants are heterozygous.

4. The process according to claim 1 wherein the crossing of step (d) is between said second parent plant and said first parental line.

5. The process according to claim 1 wherein the crossing of step (d) is between said second parental line and said first parental line.

6. The process according to claim 1 wherein said second parent plant is homozygous and the second parental line produced therefrom is obtained by cloning or inbreeding to produce said second parental line.

7. The process of claim 1 wherein cloning is achieved by vegetative propagation.

8. The process according to claim 1 wherein the pollen donor of the crossing of step (d) is derived from the pollen donor of the crossing of step (b).

9. A process for rapidly developing hybrids and commercially producing hybrid seeds in high yield, resulting in improved properties of hybrids therefrom, comprising:
   (a) crossing pairs of parent plants to produce sets of experimental original-parent-derived hybrids;

(b) selecting at least one set of optimum original-parent-derived hybrids from among said sets of experimental original-parent-derived hybrids;
(c) obtaining parental lines from each parent plant which produced the selected set of optimum original-parent-derived-hybrids by cloning any heterozygous parent plant and cloning or inbreeding any homozygous parent plant, and
(d) crossing the plants in said parental lines to produce hybrid seeds.

10. The process according to claim 9 wherein at least one of said parent plants is heterozygous.

11. The process according to claim 9 wherein both of said parent plants are heterozygous.

12. The process according to claim 9 wherein cloning is achieved by vegetative propagation.

13. The process according to claim 9 wherein the pollen donor of the crossing of step (d) is derived from the pollen donor of the crossing of step (a).

14. The process according to claims 1 or 9 wherein said plants are tomato plants.

* * * * *

UNITED STATES PATENT AND TRADEMARK OFFICE
CERTIFICATE OF CORRECTION

PATENT NO. : 4,326,358
DATED : April 27, 1982
INVENTOR(S) : Robert H. Lawrence, Jr., et. al.

It is certified that error appears in the above-indentified patent and that said Letters Patent is hereby corrected as shown below:

On the Title page, item [75],

In the Inventors Listing [75], "Tarrytwon" should read -- Tarrytown --.

In the References Cited Listing [56], reference 11, "Patterson" should read -- Gudin --.

Column 2, line 16, "F1" should read -- $F_1$ --.

Column 2, line 56, "number" should read -- numbers --.

Column 3, line 17, "F1" should read -- $F_1$ --.

Column 6, line 29, "present" should read -- parent --.

Column 10, line 3, "Brassica" should read -- *Brassica* --.

Column 12, line 36, "hypoclorite" should read -- hypochlorite --.

UNITED STATES PATENT AND TRADEMARK OFFICE
CERTIFICATE OF CORRECTION

Page 2 of 2

PATENT NO. : 4,326,358
DATED : April 27, 1982
INVENTOR(S) : Robert H. Lawrence, Jr., et. al.

It is certified that error appears in the above-indentified patent and that said Letters Patent is hereby corrected as shown below:

Column 16, line 28, "plane" should read -- plant--.

Signed and Sealed this

Nineteenth Day of October, 1993

Attest:

BRUCE LEHMAN

Attesting Officer

Commissioner of Patents and Trademarks